(12) United States Patent
Ryan

(10) Patent No.: US 6,796,194 B1
(45) Date of Patent: Sep. 28, 2004

(54) LIQUID SAMPLING DEVICE

(75) Inventor: John Ryan, San Diego, CA (US)

(73) Assignee: San Diego State University, San Diego, CA (US)

( * ) Notice: Subject to any disclaimer, the term of this patent is extended or adjusted under 35 U.S.C. 154(b) by 158 days.

(21) Appl. No.: 10/267,194

(22) Filed: Oct. 8, 2002

Related U.S. Application Data

(60) Provisional application No. 60/327,841, filed on Oct. 9, 2001.

(51) Int. Cl.⁷ ............................................. G01N 1/00
(52) U.S. Cl. .................... 73/864.31; 73/864; 73/290 R; 73/864.14; 73/863
(58) Field of Search ............................. 73/864, 864.14, 73/864.31, 863, 290 R

(56) References Cited

U.S. PATENT DOCUMENTS

| | | | |
|---|---|---|---|
| 41,652 A | 2/1864 | Terneson | 424/764 |
| 643,492 A | 2/1900 | Fromholz | 220/757 |
| 2,497,384 A | 2/1950 | Young | 220/759 |
| 2,501,940 A | 3/1950 | Hibbard | 16/425 |
| 2,624,201 A | 1/1953 | Thomson | 73/864.51 |
| 2,660,457 A | 11/1953 | Mailon | 285/7 |
| 3,329,308 A | 7/1967 | Pool | 220/752 |
| 3,686,949 A | 8/1972 | Hackett | 374/140 |
| 3,692,490 A | 9/1972 | Hall | 422/99 |
| 3,960,021 A | 6/1976 | Jones | 73/864.51 |
| 3,977,479 A * | 8/1976 | Sainsbury | 175/58 |
| 4,061,038 A | 12/1977 | Clark, Jr. | 73/427 |
| 4,112,769 A | 9/1978 | Falk | 73/864.53 |
| 4,346,613 A | 8/1982 | Turner et al. | 73/864.51 |
| 4,453,424 A | 6/1984 | Hackett | 73/864.51 |
| 4,454,775 A | 6/1984 | Ellis | 73/864.51 |
| 4,563,896 A | 1/1986 | Arnold | 73/290 R |
| 4,659,125 A | 4/1987 | Chuan | 294/19.2 |
| 4,744,256 A * | 5/1988 | Niskin | 73/864.66 |
| 4,754,656 A | 7/1988 | Charm | 73/864.63 |
| 4,979,402 A | 12/1990 | Ryan et al. | 73/863 |
| 4,982,615 A | 1/1991 | Sultan et al. | 73/864.51 |
| 4,998,000 A | 3/1991 | Halloran | 219/734 |
| 5,202,094 A | 4/1993 | Jones et al. | 422/102 |
| 5,442,970 A | 8/1995 | Hutchins | 73/864.63 |
| 5,768,940 A * | 6/1998 | Kawaguchi et al. | 73/864.41 |

FOREIGN PATENT DOCUMENTS

| | | | | |
|---|---|---|---|---|
| EP | 469427 A1 * | 2/1992 | | E21B/49/08 |
| GB | 1018829 | 2/1966 | | |

* cited by examiner

Primary Examiner—Hezron Williams
Assistant Examiner—Rodney Frank
(74) Attorney, Agent, or Firm—Morrison & Foerster LLP

(57) ABSTRACT

A sampling system includes a rocket body, and a first sampling vessel coupled to the rocket body, wherein, during operation, a propellant is discharged from the rocket body and causing the rocket body to be propelled towards a body of liquid. The sampling system may also include a deployment line coupled to the rocket body at a first point on the line, the deployment line also coupled proximate to a launching area at a second point on the line, wherein, subsequent to the discharge of the propellant, the rocket is retrieved by an operator using the deployment line.

23 Claims, 3 Drawing Sheets

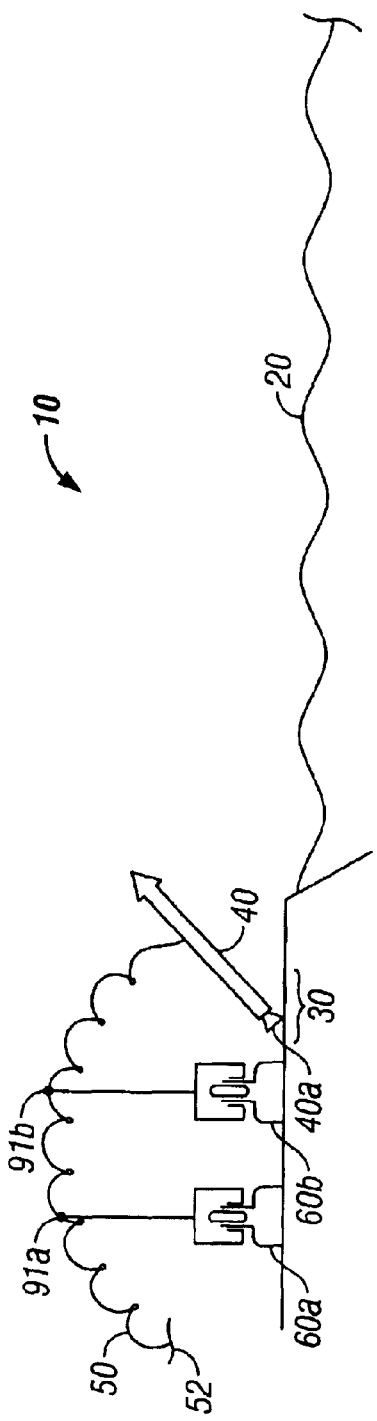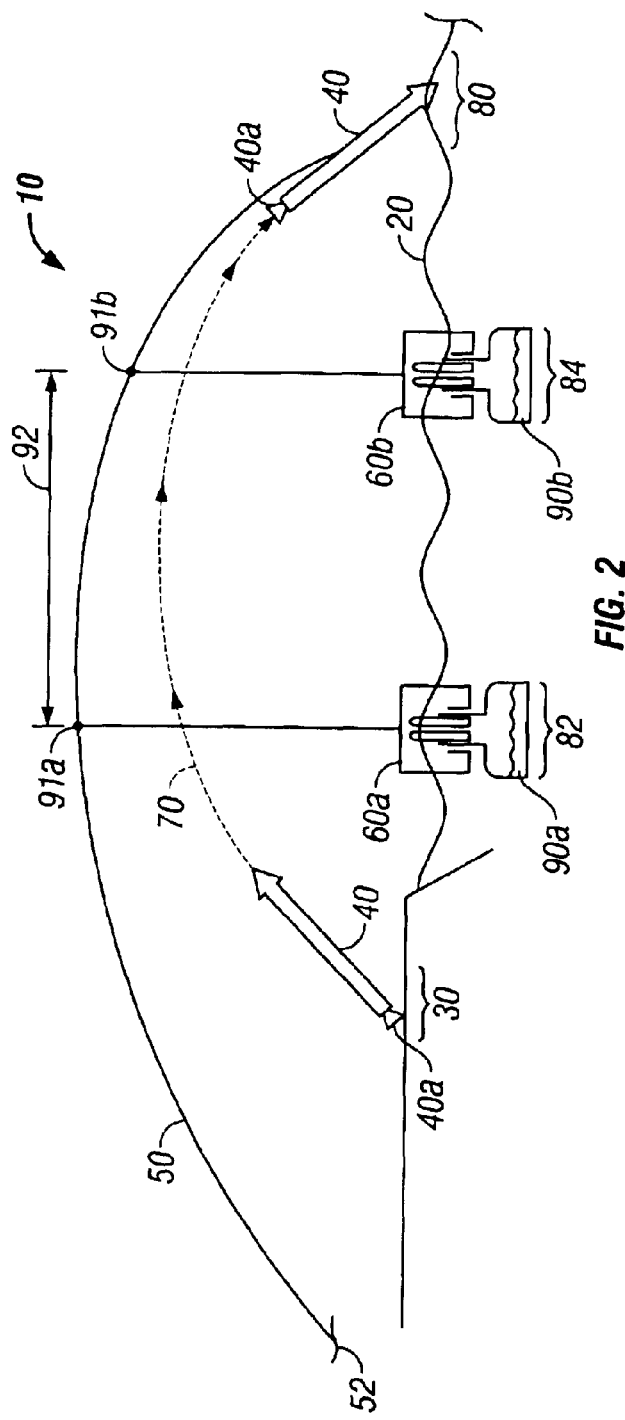

LIQUID SAMPLING DEVICE

CLAIM OF PRIORITY

This application claims priority under 35 USC §119(e) to U.S. patent application Ser. No. 60/327,841 filed on Oct. 9, 2001, the entire contents of which are hereby incorporated by reference.

TECHNICAL FIELD

This application relates to collecting liquid samples.

BACKGROUND

In order to analyze a relatively large body of liquid, such as a body of water, it may be necessary to collect samples from a variety of locations in the body of liquid. Collecting samples from a body of liquid may be performed in a variety of conventional ways. For example, a liquid sample may be collected by an operator who manually holds and dips a container into the body of liquid, or holds and dips a container attached to an end of a pole into the body of liquid.

DESCRIPTION OF THE DRAWINGS

FIG. 1 is a diagram of a sampling system before deployment.

FIG. 2 is a diagram of the sampling system of FIG. 1 after deployment.

DESCRIPTION

Figure 3:
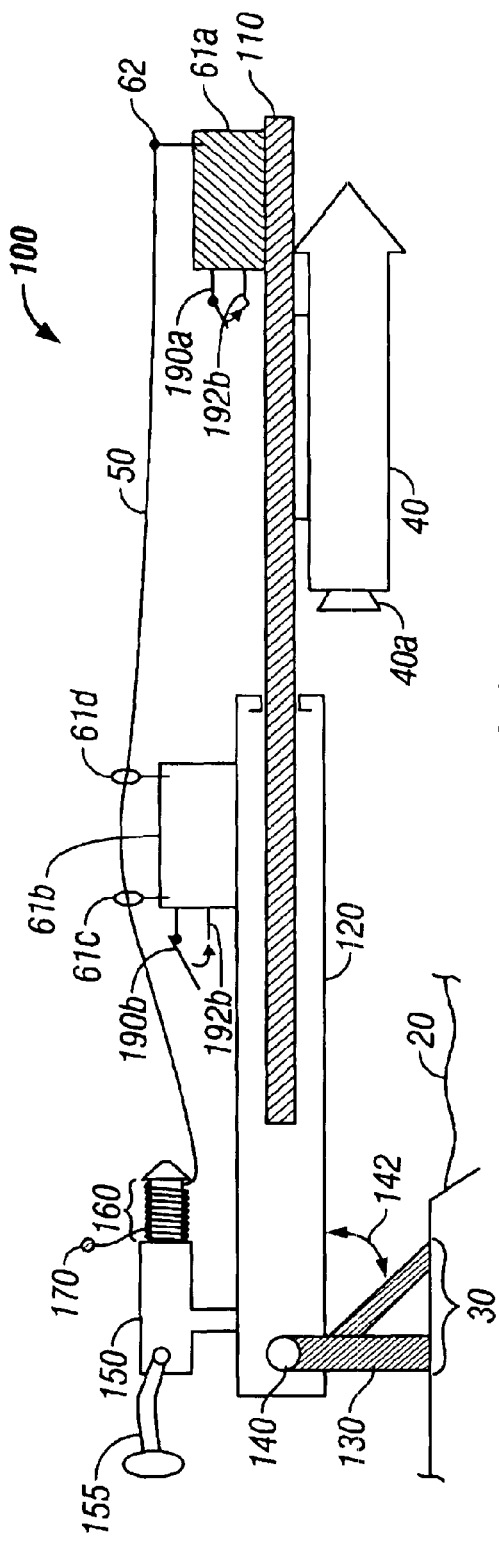
FIG. 3 is a diagram of a second embodiment of a sampling system.

Referring to FIGS. 1 and 2, sampling system 10 allows an operator of the system to collect a liquid sample from a body of liquid 20 from a relatively distant launching area 30 (in this case, launching area 30 is a beach-front location next to body of liquid 20). Sampling system 10 includes a rocket body 40 attached at one end to a deployment line 50 and held at another point 52 on the line near the launching area (or held by the operator, for example). Attached to deployment line 50 are one or more sampling vessels, in this example, vessels 60a and 60b. Vessels 60a and 60b are attached at different points on deployment line 50 so that each vessel will be filled with a liquid sample at different distances from the launching area 30, as will be explained. In operation, the operator fires rocket body 40, i.e., discharging a propellant from an exhaust 40a of rocket body 40, causing rocket body 40 to travel over body of liquid 20 along a flightpath 70 (see FIG. 2) and eventually splash down into body of liquid 20 at a splashdown area 80. As rocket body 40 travels away from launching area 30 it pulls attached deployment line 50, and attached vessels 60a and 60b, along flightpath 70 behind rocket body 40. Each of the attached vessels 60a and 60b splash down in sampling areas 82 and 84, respectively, and begin filling with liquid samples 90a and 90b, respectively. When vessels 60a and 60b have filled (at least partially), the operator may retrieve vessels 60a and 60b (and their respective liquid samples 90a and 90b) and rocket body 40 by pulling deployment line 50 back to launching area 30. A separation distance 92 between sampling splashdown areas 82 and 84 is established by connecting vessels 60a and 60b at two different points 91a and 91b, respectively, on deployment line 50. Therefore, the operator may control separation distance 92 where samples are obtained by connecting each vessel at different points on line 50. This way of collecting liquid samples allows an operator to collect samples at a relatively long distance from the operator. Moreover, this way of collecting liquid samples allows an operator to collect samples from an area in a body of liquid which is not amenable to manual collection of samples, for example, a coastal area that may experience high surf, undertow, etc.

In an embodiment of system 10, the propellant used to propel rocket body 40 is a charge of compressed air. Using compressed air as the propellant for rocket body 40 is advantageous since the rocket body may be stored safely, without a compressed air charge, when not in use. Moreover, releasing compressed air does not introduce contaminants into the atmosphere during flight, or into the body of liquid being sampled after splashdown, as may be the case if using conventional (e.g., petroleum based) propellants.

Referring to FIG. 3, a second embodiment of a sampling system 100 is shown positioned at a launching area 30 next to body of liquid 20. Sampling system 100 includes a rod 110 attached along one longitudinal surface of rod 110 to a longitudinal surface of rocket body 40. In this example of system 100, rod 110 is slid into one end of a launching tube 120. Launching tube 120 is coupled by bearing 140 to an upright 130, allowing tube 120 to pivot 142 up and down. In use, an operator pivots launching tube 120 on bearing 140 to control the flightpath of rocket body 40/rod 110. This example of system 110 also includes a "fishing" type reel 150 having a handle 155 and a spool 160 onto which deployment line 50 is wound on and off. In this example of system 100, a second sampling vessel 61b rests on top of launching tube 120 before firing rocket body 40. Deployment line 50 passes through two eyelets 61c and 61d attached at opposite ends of vessel 61b. A ball 170 is attached at a point on deployment line 50. In use, an operator fires rocket body 40/rod 110 away from launching area 30. As rocket body 40/rod 110 travels away from launching area 30, deployment line 50 is pulled off reel 150 until attached ball 170 contacts either of the two eyelets 61c or 61d of vessel 61b. At this point vessel 61b is pulled along behind rocket 40/rod 110 until rocket body 40/rod 110 splashs down in area 80 and vessel 61b splashs down in a sampling area between area 80 and launching area 30 (not shown). The operator may then retrieve rocket body 40/rod 110 (and attached vessel 61a) and vessel 61b by reeling in deployment line 50 by cranking handle 155 of reel 150 (i.e., winding deployment line 50 back onto spool 160).

In this embodiment, vessels 61a and 61b each include a hinged lid 190a and 190b, respectively, that is closed by the flow of liquid passing by each vessel as they are pulled back using deployment line 50. In an embodiment, hinged lid 190a and 190b are held in a closed position by a pressure clasp 192a and 192b, respectively.

Figure 4:
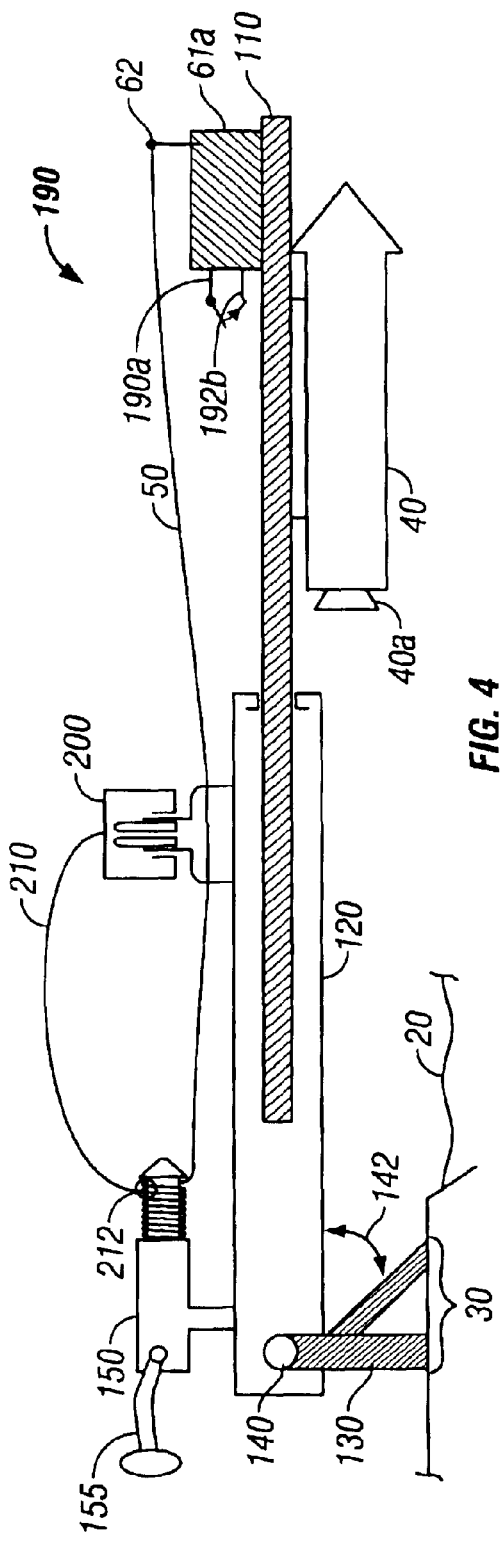
FIG. 4 is a diagram of third embodiment of a sampling system.
Figure 5:
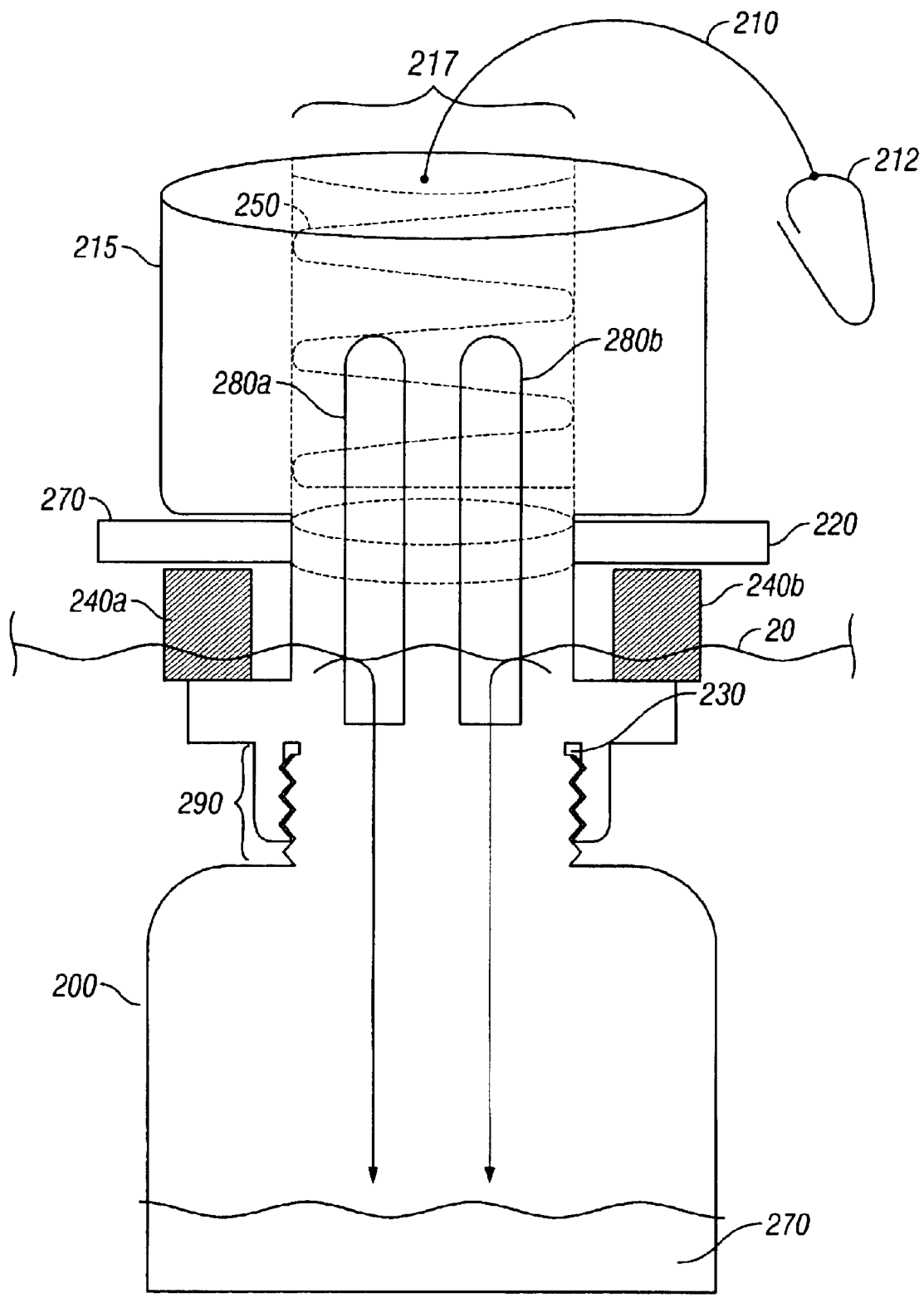
FIG. 5 is a diagram of a sampling vessel.

Referring to FIGS. 4 and 5, a third embodiment of a sampling system 190 is shown. Operation of system 190 is similar to that previously described for system 100. However, system 190 differs from system 100 (see FIG. 3) in the way that second sampling vessel, 200, is attached to deployment line 50, as will be explained. In system 190, a first sampling vessel 61a is attached to a first end of rod 110, and second sampling vessel 200 is attached by lanyard 210 (e.g., a relatively short line) and clip 212 to a point on deployment line 50. After rocket 40/rod 110 is fired from launching area 30, deployment line 50 is un-wound from reel 150 and vessel 200 is eventually "caught" by clip 212 on line 50, pulling vessel 200 towards body of liquid 20.

In an embodiment, additional sampling vessels, similar to vessel 200, could also be attached to line 50, at various points on line 50, so that additional liquid samples could be gathered during a single use of system 190. In more detail, still referring to FIG. 5, two or more sampling vessels similar to vessel 200, each including a lanyard 210, and a clip 212, are attached at different points on deployment line 50 before rocket 40/rod 110 is launched. After rocket 40/rod 110 is launched, the two or more vessels 200 are pulled behind rocket 40/rod 110 as deployment line 50 is un-wound from reel 150 until line 50 reaches the attachment points of each clip 212, causing each respective vessel to splash into the body of liquid at different points between launching area 30 and splashdown area 80.

Still referring to FIG. 5, in an embodiment, sampling vessel 200 includes a cap 215 having a hollow center area 217. Within hollow area 217 a lid 220 is held above a top rim 230 of vessel 200 by dissolvable elements 240*a* and 240*b*. A spring 250 is mounted between lid 220 and a top of cap 260, the dissolvable elements 240*a* and 240*b* holding spring 250 in a compressed state. When vessel 200 is placed in body of liquid 20, a sample 270 of the liquid enters cap 215 through inlets 280*a* and 280*b* formed in a side of cap 215. While sample 270 is entering vessel 200, liquid from the body of liquid 20 begins to dissolve elements 240*a* and 240*b*. Eventually, elements 240*a* and 240*b* dissolve sufficiently to allow spring 250 to expand and move lid 220 against rim 230 of vessel 200, and sealing sample 270 in vessel 200. In this embodiment, varying the size, shape and/or the constituent materials of dissolvable elements 240*a* and 240*b* allows an adjustment of a closing time of lid 220 onto rim 230 (i.e., the amount of time after vessel 200 contacts a body of liquid 20 before vessel 200 is closed by lid 220).

In an embodiment, cap 215 is attached to vessel 200 by a threaded connection 290.

In an embodiment, at least one of the dissolvable elements is made from vegetable-based or sea-weed based material.

In an embodiment, one or more of the sampling vessels are shaped to reduce air resistance during flight.

In an embodiment, the distance between launching area 30 and splashdown area 80 is controlled by the operator, for example, by adjusting a quantity of propellent (e.g.), or an amount (or pressure) of a compressed air charge placed into rocket body 40, or by altering the firing angle of the rocket body before firing.

The invention is not limited to the specific embodiments described above. For example, we mentioned using compressed air as the propellant system for the rocket, however, other rocket propellants could be used. Also, we discussed the possibility of an operator gathering a plurality of samples with each use of the various systems, however, a single sample could be gathered using a single sampling vessel coupled either to the rocket body or the deployment line, for example. We also described the launching area as a coastal area, such as a beach area. However, the embodiments described could also be operated from a launching area on a floating vessel (e.g., a boat or barge). We also described a sampling vessel 200 that includes two dissolvable elements. However, in another embodiment, a single dissolvable element could be used.

Other embodiments not described herein are also within the scope of the following claims.

What is claimed is:

1. A method comprising:

firing a rocket from a launching area towards a body of liquid;

collecting a sample of liquid from the body of water in a first vessel coupled to the rocket; and retrieving the first vessel.

2. The method of claim 1, wherein the first vessel is connected to the rocket.

3. The method of claim 1, wherein firing further comprises:

firing a rocket body coupled to a line held at the launching area.

4. The method of claim 3, wherein collecting further comprises:

collecting a plurality of samples of liquid, wherein each of the plurality of samples are collected in a corresponding plurality of vessels spaced apart from each other.

5. The method of claim 4, wherein at least one of the plurality of vessels is coupled to the line.

6. The method of claim 4, wherein at least one of the plurality of vessels is coupled to the line by a clip connection.

7. The method of claim 1, wherein firing further comprises:

firing a rocket body coupled to a line, the line wound onto a reel, wherein firing causes the rocket body to un-wind the line from the reel.

8. The method of claim 7, wherein retrieving further comprises:

winding the line back onto the reel.

9. The method of claim 1, wherein firing further comprises:

discharging a charge of compressed air from the rocket body.

10. The method of claim 9, wherein the launching area comprises an area of land proximate to the body of liquid.

11. The method of claim 9, wherein the launching area comprises a surface of a floating vessel.

12. The method of claim 1, wherein collecting further comprises:

collecting a sample using a vessel having a hinged lid.

13. The method of claim 1, wherein collecting further comprises:

collecting a sample using a vessel having a lid held open by a dissolvable element.

14. A sampling system comprising:

a rocket body; and a first sampling vessel coupled to the rocket body, wherein, during operation of the system, a propellant is discharged from the rocket body and causing the rocket body to be propelled towards a body of liquid.

15. The sampling system of claim 14, further comprising:

a deployment line coupled to the rocket body at a first point on the line, the deployment line also coupled proximate to a launching area at a second point on the line, wherein, subsequent to the discharge of the propellant, the rocket is retrieved by an operator using the deployment line.

16. The system of claim 15, further comprising:

a second sampling vessel coupled to the line, wherein during operation of the system, the second sampling vessel is pulled by the line into the body of liquid at a point between a splashdown area of the rocket body and the launching area.

17. The system of claim 16, wherein the second sampling vessel is attached to the line using a clip attachment.

18. The system of claim 15, further comprising:
a reel, wherein the line is un-wound from the reel when the rocket body is in flight, and wound back onto the reel subsequent to the splashdown of the rocket body into the body of liquid.

19. The system of claim 15, wherein the first sampling vessel further comprises:
a lid held open by at least one dissolvable element.

20. The system of claim 15, wherein the first sampling vessel further comprises:
a hinged lid that is closable by a flow of water against the lid.

21. The system of claim 14, wherein the propellant comprises a charge of compressed air.

22. The system of claim 15, further comprising:
a rod connected along one longitudinal surface of the rod to one longitudinal surface of the rocket body.

23. The system of claim 22, further comprising:
a launching tube pivotally connected to an up-right positioned proximate to the launching area,
wherein, during operation of the system, the rod is inserted into the tube and tube is pivoted to adjust a launching angle of the rocket body and rod.

* * * * *